US009752827B2

(12) United States Patent
Valencia (10) Patent No.: US 9,752,827 B2
(45) Date of Patent: Sep. 5, 2017

(54) METHOD AND SYSTEM OF MAINTAINING A LIQUID LEVEL IN A DISTILLATION TOWER (71) Applicant: Jaime A. Valencia, Houston, TX (US)

(72) Inventor: Jaime A. Valencia, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 218 days.

(21) Appl. No.: 14/516,686

(22) Filed: Oct. 17, 2014

(65) Prior Publication Data

US 2015/0159939 A1 Jun. 11, 2015

Related U.S. Application Data (60) Provisional application No. 61/912,959, filed on Dec. 6, 2013.

(51) Int. Cl.
*F25J 3/00* (2006.01)
*F25J 1/00* (2006.01)
(Continued)

(52) U.S. Cl.
CPC .......... *F25J 3/0266* (2013.01); *B01D 3/324* (2013.01); *C07C 7/05* (2013.01); *F25J 1/0022* (2013.01);
(Continued)

(58) Field of Classification Search
CPC ........ F25J 3/0209; F25J 3/0233; F25J 3/0266; F25J 2280/40; F25J 2205/20;
(Continued)

(56) References Cited

U.S. PATENT DOCUMENTS 2,621,216 A 12/1952 White .................. 260/683.3
2,843,219 A 7/1958 Habgood ............. 183/114.2
(Continued)

FOREIGN PATENT DOCUMENTS

DE 3149847 7/1983 ............ B01D 5/00
EP 0133208 2/1985 ............ B01D 53/14
(Continued)

OTHER PUBLICATIONS

U.S. Appl. No. 14/516,686, filed Oct. 17, 2014, Valencia, J. A.
(Continued)

*Primary Examiner* — Keith Raymond
(74) *Attorney, Agent, or Firm* — ExxonMobil Upstream Research Company—Law Department (57) ABSTRACT The present disclosure provides a distillation tower that may include a stripper section constructed and arranged to separate a feed stream at a temperature and pressure at which the feed stream forms no solid; a controlled freeze zone section constructed and arranged to separate the feed stream at a temperature and pressure at which the feed stream forms a solid; a melt tray assembly in the controlled freeze zone section that includes a liquid; an underflow weir in the controlled freeze zone section that alters a flow of the liquid in the melt tray assembly; an overflow weir in the controlled freeze zone section that works with the underflow weir to alter the flow of the liquid in the melt tray assembly and is adjacent to the underflow weir; and a covering element in the controlled freeze zone section that is connected to and extends from the underflow weir.

10 Claims, 6 Drawing Sheets (51) Int. Cl.
*F25J 3/02* (2006.01)
*F25J 3/06* (2006.01)
*B01D 3/32* (2006.01)
*C07C 7/05* (2006.01)
*F25J 3/08* (2006.01)
*C10L 3/10* (2006.01)

(52) U.S. Cl.
CPC ........... *F25J 1/0027* (2013.01); *F25J 3/0209* (2013.01); *F25J 3/0233* (2013.01); *F25J 3/061* (2013.01); *F25J 3/067* (2013.01); *F25J 3/0635* (2013.01); *F25J 3/08* (2013.01); *C10L 3/101* (2013.01); *C10L 2290/543* (2013.01); *C10L 2290/545* (2013.01); *C10L 2290/58* (2013.01); *F25J 2200/02* (2013.01); *F25J 2200/30* (2013.01); *F25J 2200/50* (2013.01); *F25J 2200/74* (2013.01); *F25J 2200/90* (2013.01); *F25J 2205/04* (2013.01); *F25J 2205/20* (2013.01); *F25J 2220/66* (2013.01); *F25J 2235/60* (2013.01); *F25J 2280/40* (2013.01); *F25J 2290/12* (2013.01); *F25J 2290/40* (2013.01); *Y02C 10/12* (2013.01)

(58) Field of Classification Search
CPC .. F25J 2200/74; F25J 2220/66; F25J 2200/90; F25J 3/04903; Y02C 10/12; C10L 3/104; B01D 3/20; B01D 3/205; B01D 3/22; B01D 3/24
USPC .................................................... 62/602, 929
See application file for complete search history.

(56) References Cited

U.S. PATENT DOCUMENTS

| | | | |
|---|---|---|---|
| 2,863,527 A | 12/1958 | Herbert et al. | 183/115 |
| 2,960,837 A | 11/1960 | Swenson et al. | 62/24 |
| 3,050,950 A | 8/1962 | Karwat et al. | 62/13 |
| 3,109,726 A | 11/1963 | Karwat | 62/13 |
| 3,282,576 A * | 11/1966 | Bruckert | B01D 3/22 261/114.1 |
| 3,349,571 A | 10/1967 | Nebgen | 62/23 |
| 3,393,527 A | 7/1968 | Swensen et al. | 62/16 |
| 3,400,512 A | 9/1968 | McKay | 55/69 |
| 3,421,984 A | 1/1969 | Jensen et al. | 203/41 |
| 3,683,634 A | 8/1972 | Streich | 62/29 |
| 3,705,625 A | 12/1972 | Whitten et al. | 166/252 |
| 3,767,766 A | 10/1973 | Tjoa et al. | 423/220 |
| 3,824,080 A | 7/1974 | Smith et al. | 23/288 |
| 3,842,615 A | 10/1974 | Reigel et al. | 62/171 |
| 3,848,427 A | 11/1974 | Loofbourow | 62/260 |
| 3,895,101 A | 7/1975 | Tsuruta | 423/574 |
| 3,929,635 A | 12/1975 | Buriks et al. | 210/54 |
| 3,933,001 A | 1/1976 | Muska | 62/47 |
| 4,129,626 A | 12/1978 | Mellbom | 261/114 |
| 4,246,015 A | 1/1981 | Styring | 62/12 |
| 4,270,937 A | 6/1981 | Adler | 62/17 |
| 4,280,559 A | 7/1981 | Best | 166/303 |
| 4,281,518 A | 8/1981 | Muller et al. | 62/12 |
| 4,318,723 A | 3/1982 | Holmes et al. | 62/20 |
| 4,319,964 A | 3/1982 | Katz et al. | 202/172 |
| 4,336,233 A | 6/1982 | Appl et al. | 423/228 |
| 4,344,485 A | 8/1982 | Butler | 166/271 |
| 4,370,156 A | 1/1983 | Goddin et al. | 62/17 |
| 4,382,912 A | 5/1983 | Madgavkar et al. | 423/224 |
| 4,383,841 A | 5/1983 | Ryan et al. | 62/17 |
| 4,405,585 A | 9/1983 | Sartori et al. | 423/228 |
| 4,417,449 A | 11/1983 | Hegarty et al. | 62/28 |
| 4,417,909 A | 11/1983 | Weltmer | 62/12 |
| 4,421,535 A | 12/1983 | Mehra | 62/17 |
| 4,441,900 A | 4/1984 | Swallow | 62/29 |
| 4,459,142 A | 7/1984 | Goddin | 62/17 |
| 4,462,814 A | 7/1984 | Holmes et al. | 62/17 |
| 4,466,946 A | 8/1984 | Goddin et al. | 423/228 |
| 4,511,382 A | 4/1985 | Valencia et al. | 62/20 |
| 4,512,782 A | 4/1985 | Bauer et al. | 55/48 |
| 4,533,372 A | 8/1985 | Valencia et al. | 62/12 |
| 4,551,158 A | 11/1985 | Wagner et al. | 55/46 |
| 4,563,202 A | 1/1986 | Yao et al. | 62/17 |
| 4,592,766 A | 6/1986 | Kumman et al. | 62/18 |
| 4,602,477 A | 7/1986 | Lucadamo | 62/24 |
| 4,609,388 A | 9/1986 | Adler et al. | 62/12 |
| 4,636,334 A | 1/1987 | Skinner et al. | 252/377 |
| 4,695,672 A | 9/1987 | Bunting | 585/867 |
| 4,697,642 A | 10/1987 | Vogel | 166/263 |
| 4,710,213 A | 12/1987 | Sapper et al. | 62/28 |
| 4,717,408 A | 1/1988 | Hopewell | 62/20 |
| 4,720,294 A | 1/1988 | Lucadamo et al. | 62/31 |
| 4,747,858 A | 5/1988 | Gottier | 62/17 |
| 4,761,167 A | 8/1988 | Nicholas et al. | 62/17 |
| 4,762,543 A | 8/1988 | Pantermuehl et al. | 62/28 |
| 4,769,054 A | 9/1988 | Steigman | 62/12 |
| 4,822,393 A | 4/1989 | Markbreiter et al. | 62/17 |
| 4,831,206 A | 5/1989 | Zarchy | 585/737 |
| 4,923,493 A | 5/1990 | Valencia et al. | 62/13 |
| 4,927,498 A | 5/1990 | Rushmere | 162/168.3 |
| 4,935,043 A | 6/1990 | Blanc et al. | 62/20 |
| 4,954,220 A | 9/1990 | Rushmere | 162/168.3 |
| 4,972,676 A | 11/1990 | Sakai | 62/18 |
| 4,976,849 A | 12/1990 | Soldati | 208/351 |
| 5,011,521 A | 4/1991 | Gottier | 62/11 |
| 5,062,270 A | 11/1991 | Haut et al. | 62/12 |
| 5,120,338 A | 6/1992 | Potts et al. | 62/12 |
| 5,137,550 A | 8/1992 | Hegarty et al. | 55/43 |
| 5,152,927 A | 10/1992 | Rivers | 252/344 |
| 5,233,837 A | 8/1993 | Callahan | 62/38 |
| 5,240,472 A | 8/1993 | Sircar | 95/52 |
| 5,247,087 A | 9/1993 | Rivers | 544/357 |
| 5,265,428 A * | 11/1993 | Valencia | B01D 3/18 202/158 |
| 5,335,504 A | 8/1994 | Durr et al. | 62/20 |
| 5,345,771 A | 9/1994 | Dinsmore | 62/18 |
| 5,567,396 A | 10/1996 | Perry et al. | 422/190 |
| 5,620,144 A | 4/1997 | Strock et al. | 239/557 |
| 5,643,460 A | 7/1997 | Marble et al. | 210/705 |
| 5,700,311 A | 12/1997 | Spencer | 95/236 |
| 5,720,929 A | 2/1998 | Minkkinen et al. | 422/190 |
| 5,819,555 A | 10/1998 | Engdahl | 62/637 |
| 5,820,837 A | 10/1998 | Marjanovich et al. | 423/220 |
| 5,899,274 A | 5/1999 | Frauenfeld et al. | 166/401 |
| 5,956,971 A | 9/1999 | Cole et al. | 62/623 |
| 5,964,985 A | 10/1999 | Wootten | 201/40 |
| 5,983,663 A | 11/1999 | Sterner | 62/620 |
| 6,053,007 A | 4/2000 | Victory et al. | 62/619 |
| 6,053,484 A | 4/2000 | Fan et al. | 261/114.1 |
| 6,082,133 A | 7/2000 | Barclay et al. | 62/619 |
| 6,082,373 A | 7/2000 | Sakurai et al. | 134/1 |
| 6,162,262 A | 12/2000 | Minkkinen et al. | 23/295 |
| 6,223,557 B1 | 5/2001 | Cole | 62/613 |
| 6,240,744 B1 | 6/2001 | Agrawal et al. | 62/643 |
| 6,267,358 B1 | 7/2001 | Gohara et al. | 261/110 |
| 6,270,557 B1 | 8/2001 | Millet et al. | 95/96 |
| 6,274,112 B1 | 8/2001 | Moffett et al. | 423/338 |
| 6,287,367 B1 * | 9/2001 | Buchanan | B01D 3/20 261/113 |
| 6,336,334 B1 | 1/2002 | Minkkinen et al. | 62/123 |
| 6,374,634 B2 | 4/2002 | Gallarda et al. | 62/620 |
| 6,401,486 B1 | 6/2002 | Lee et al. | 62/630 |
| 6,416,729 B1 | 7/2002 | DeBerry et al. | 423/573.1 |
| 6,442,969 B1 | 9/2002 | Rojey et al. | 62/618 |
| 6,500,982 B1 | 12/2002 | Hale et al. | 562/600 |
| 6,505,683 B2 | 1/2003 | Minkkinen et al. | 166/266 |
| 6,516,631 B1 | 2/2003 | Trebble | 62/630 |
| 6,517,801 B2 | 2/2003 | Watson et al. | 423/574.1 |
| 6,539,747 B2 | 4/2003 | Minta et al. | 62/620 |
| 6,565,629 B1 | 5/2003 | Hayashida et al. | 95/211 |
| 6,605,138 B2 | 8/2003 | Frondorf | 95/160 |
| 6,631,626 B1 | 10/2003 | Hahn | 62/612 |
| 6,632,266 B2 | 10/2003 | Thomas et al. | 95/49 |
| 6,662,872 B2 | 12/2003 | Gutek et al. | 166/272.4 |
| 6,708,759 B2 | 3/2004 | Leaute et al. | 166/272.4 |
| 6,711,914 B2 | 3/2004 | Lecomte | 62/625 |

(56) References Cited

U.S. PATENT DOCUMENTS

| | | |
|---|---|---|
| 6,735,979 B2 | 5/2004 | Lecomte et al. ............... 62/611 |
| 6,755,251 B2 | 6/2004 | Thomas et al. ............... 166/265 |
| 6,755,965 B2 | 6/2004 | Pironti et al. ............... 208/347 |
| 6,818,194 B2 | 11/2004 | DeBerry et al. ............... 423/228 |
| 6,883,327 B2 | 4/2005 | Iijima et al. ............... 60/649 |
| 6,946,017 B2 | 9/2005 | Leppin et al. ............... 95/139 |
| 6,958,111 B2 | 10/2005 | Rust et al. ............... 202/158 |
| 6,962,061 B2 | 11/2005 | Wilding et al. ............... 62/613 |
| 7,001,490 B2 | 2/2006 | Wostbrock et al. ............... 203/1 |
| 7,004,985 B2 | 2/2006 | Wallace et al. ............... 48/198.3 |
| 7,066,986 B2 | 6/2006 | Haben et al. ............... 95/99 |
| 7,073,348 B2 | 7/2006 | Clodic et al. ............... 62/532 |
| 7,121,115 B2 | 10/2006 | Lemaire et al. ............... 62/625 |
| 7,128,150 B2 | 10/2006 | Thomas et al. ............... 166/266 |
| 7,128,276 B2 | 10/2006 | Nilsen et al. ............... 236/124 |
| 7,152,431 B2 | 12/2006 | Amin et al. ............... 62/637 |
| 7,211,128 B2 | 5/2007 | Thomas et al. ............... 95/135 |
| 7,211,701 B2 | 5/2007 | Muller et al. ............... 568/853 |
| 7,219,512 B1 | 5/2007 | Wilding et al. ............... 62/617 |
| 7,285,225 B2 | 10/2007 | Copeland et al. ............... 210/785 |
| 7,325,415 B2 | 2/2008 | Amin et al. ............... 62/541 |
| 7,424,808 B2 | 9/2008 | Mak ............... 62/625 |
| 7,437,889 B2 | 10/2008 | Roberts et al. ............... 62/619 |
| 7,442,231 B2 | 10/2008 | Landrum ............... 95/45 |
| 7,442,233 B2 | 10/2008 | Mitariten ............... 95/123 |
| 7,493,779 B2 | 2/2009 | Amin ............... 62/617 |
| 7,536,873 B2 | 5/2009 | Nohlen ............... 62/644 |
| 7,550,064 B2 | 6/2009 | Bassler et al. ............... 203/29 |
| 7,575,624 B2 | 8/2009 | Cartwright et al. ............... 95/51 |
| 7,597,746 B2 | 10/2009 | Mak et al. ............... 95/169 |
| 7,635,408 B2 | 12/2009 | Mak et al. ............... 95/187 |
| 7,637,984 B2 | 12/2009 | Adamopoulos ............... 95/45 |
| 7,637,987 B2 | 12/2009 | Mak ............... 95/160 |
| 7,641,717 B2 | 1/2010 | Gal ............... 95/187 |
| 7,662,215 B2 | 2/2010 | Sparling et al. ............... 95/172 |
| 7,691,239 B2 | 4/2010 | Kister et al. ............... 203/2 |
| 7,722,289 B2 | 5/2010 | Leone et al. ............... 405/53 |
| 7,729,976 B2 | 6/2010 | Hill et al. ............... 705/37 |
| 7,770,872 B2 | 8/2010 | Delatour ............... 261/110 |
| 7,795,483 B2 | 9/2010 | Kulprathipanja et al. ............... 585/24 |
| 7,806,965 B2 | 10/2010 | Stinson ............... 95/187 |
| 7,814,975 B2 | 10/2010 | Hagen et al. ............... 166/257 |
| 7,879,135 B2 | 2/2011 | Ravikumar et al. ............... 95/11 |
| 7,901,583 B2 | 3/2011 | McColl et al. ............... 210/710 |
| 7,955,496 B2 | 6/2011 | Iqbal et al. ............... 208/129 |
| 8,002,498 B2 | 8/2011 | Leone et al. ............... 405/53 |
| 8,020,408 B2 | 9/2011 | Howard et al. ............... 62/646 |
| 8,133,764 B2 | 3/2012 | Dirks et al. ............... 438/124 |
| 8,136,799 B2 | 3/2012 | Griepsma ............... 261/114.5 |
| 8,303,685 B2 | 11/2012 | Schubert et al. ............... 95/181 |
| 8,308,849 B2 | 11/2012 | Gal ............... 95/187 |
| 8,312,738 B2 | 11/2012 | Singh et al. ............... 62/629 |
| 8,372,169 B2 | 2/2013 | Tsangaris et al. ............... 48/120 |
| 8,381,544 B2 | 2/2013 | Coyle ............... 62/618 |
| 8,388,832 B2 | 3/2013 | Moffett et al. ............... 208/390 |
| 8,428,835 B2 | 4/2013 | Habert et al. ............... 701/54 |
| 8,475,572 B2 | 7/2013 | Prast et al. ............... 95/269 |
| 8,500,105 B2 | 8/2013 | Nieuwoudt ............... 261/79.2 |
| 8,529,662 B2 | 9/2013 | Kelley et al. ............... 95/96 |
| 2002/0174687 A1 | 11/2002 | Cai ............... 65/158 |
| 2002/0189443 A1 | 12/2002 | McGuire ............... 95/32 |
| 2003/0181772 A1 | 9/2003 | Meyer et al. ............... 585/324 |
| 2006/0207946 A1 | 9/2006 | McColl et al. ............... 210/733 |
| 2006/0239879 A1 | 10/2006 | Lallemand et al. ............... 423/220 |
| 2007/0056317 A1 | 3/2007 | Amin et al. ............... 62/532 |
| 2007/0144943 A1 | 6/2007 | Lemaire et al. ............... 208/208 |
| 2007/0277674 A1 | 12/2007 | Hirano et al. ............... 95/290 |
| 2008/0034789 A1 | 2/2008 | Fieler et al. ............... 62/623 |
| 2008/0091316 A1 | 4/2008 | Szczublewski ............... 701/36 |
| 2008/0092589 A1 | 4/2008 | Tranier et al. ............... 62/640 |
| 2008/0150171 A1* | 6/2008 | Lee ............... B01D 3/20 261/114.1 |
| 2008/0307827 A1 | 12/2008 | Hino et al. ............... 62/634 |
| 2009/0023605 A1 | 1/2009 | Lebl et al. ............... 506/27 |
| 2009/0220406 A1 | 9/2009 | Rahman ............... 423/437.1 |
| 2010/0011809 A1 | 1/2010 | Mak ............... 62/620 |
| 2010/0018248 A1* | 1/2010 | Fieler ............... F25J 3/0209 62/617 |
| 2010/0024472 A1 | 2/2010 | Amin et al. ............... 62/541 |
| 2010/0064725 A1 | 3/2010 | Chieng et al. ............... 62/620 |
| 2010/0107687 A1 | 5/2010 | Andrian et al. ............... 62/620 |
| 2010/0132405 A1 | 6/2010 | Nilsen ............... 62/611 |
| 2010/0147022 A1 | 6/2010 | Hart et al. ............... 62/601 |
| 2010/0187181 A1 | 7/2010 | Sortwell ............... 210/726 |
| 2010/0310439 A1 | 12/2010 | Brok et al. ............... 423/222 |
| 2011/0132034 A1 | 6/2011 | Beaumont et al. ............... 62/620 |
| 2011/0154856 A1 | 6/2011 | Andrian et al. ............... 62/618 |
| 2011/0168019 A1 | 7/2011 | Northrop et al. ............... 95/186 |
| 2011/0192190 A1 | 8/2011 | Andrian et al. ............... 62/617 |
| 2011/0265512 A1 | 11/2011 | Bearden et al. ............... 62/617 |
| 2012/0006055 A1 | 1/2012 | Van Santen et al. ............... 62/618 |
| 2012/0031143 A1 | 2/2012 | Van Santem et al. ............... 62/617 |
| 2012/0031144 A1 | 2/2012 | Northrop et al. ............... 62/617 |
| 2012/0079852 A1 | 4/2012 | Northrop et al. ............... 62/620 |
| 2012/0125043 A1 | 5/2012 | Cullinane et al. ............... 62/620 |
| 2012/0204599 A1 | 8/2012 | Northrop et al. ............... 62/617 |
| 2012/0279728 A1 | 11/2012 | Northrop et al. ............... 166/401 |
| 2013/0032029 A1 | 2/2013 | Mak ............... 95/94 |
| 2013/0074541 A1 | 3/2013 | Kaminsky et al. ............... 62/601 |
| 2013/0098105 A1 | 4/2013 | Northrop ............... 62/617 |
| 2014/0137599 A1 | 5/2014 | Oelfke et al. ............... 62/619 |

FOREIGN PATENT DOCUMENTS

| | | | |
|---|---|---|---|
| EP | 0508244 | 10/1992 | ............ B01D 53/34 |
| EP | 1338557 | 3/2005 | ............ C01B 17/04 |
| GB | 1010403 | 11/1965 | |
| WO | WO 02/32536 | 4/2002 | ............ B01F 13/00 |
| WO | WO 02/39038 | 5/2002 | ............ F25J 3/06 |
| WO | WO 2004/047956 | 6/2004 | ............ B01D 53/14 |
| WO | WO 2008/034789 | 3/2008 | ............ G10K 11/00 |
| WO | WO 2008/095258 | 8/2008 | ............ F25J 3/02 |
| WO | WO 2008/152030 | 12/2008 | ............ B01D 53/00 |
| WO | WO 2009/023605 | 2/2009 | |
| WO | WO 2009/029353 | 3/2009 | ............ E21B 43/00 |
| WO | WO 2009/087206 | 7/2009 | ............ B01D 53/00 |
| WO | WO 2010/023238 | 3/2010 | ............ F25J 3/06 |
| WO | WO 2010/052299 | 5/2010 | ............ B01D 53/00 |
| WO | WO 2010/136442 | 12/2010 | ............ B01D 53/00 |
| WO | WO 2011/026170 | 3/2011 | ............ C10L 3/10 |
| WO | WO 2013/095828 | 6/2013 | ............ B01D 53/00 |
| WO | WO 2013/142100 | 9/2013 | ............ B03C 3/00 |

OTHER PUBLICATIONS

U.S. Appl. No. 14/516,689, filed Oct. 17, 2014, Cullinane, J. T. et al.
U.S. Appl. No. 14/516,705, filed Oct. 17, 2014, Valencia, J. A. et al.
U.S. Appl. No. 14/516,709, filed Oct. 17, 2014, Valencia, J. A.
U.S. Appl. No. 14/516,713, filed Oct. 17, 2014, Valencia, J. A. et al.
U.S. Appl. No. 14/516,717, filed Oct. 17, 2014, Valencia, J. A. et al.
U.S. Appl. No. 14/516,718, filed Oct. 17, 2014, Valencia, J. A.
U.S. Appl. No. 14/516,726, filed Oct. 17, 2014, Valencia, J. A. et al.
U.S. Appl. No. 14/516,731, filed Oct. 17, 2014, Valencia, J. A. et al.
Aaron, D. et al. (2005) "Separation of $CO_2$ from Flue Gas: A Review," *Separation Science and Technology*, 40, pp. 321-348.
Amin, R. (2003) "Advanced Mini Natural Gas Liquefier," *LNG Journal*, Mar.-Apr. 2003, pp. 20-23.
Black, S. (2006) "Chilled Ammonia Process for CO2 Capture," *Alstom Position Paper*, Nov. 2006, 6 pgs.
Ciulla, Vincent (2007) "How the Engine Works," About.com, Mar. 21, 2007, [retrieved from the internet on Aug. 17, 2012]. <URL: http://autorepair.about.com/cs/generalinfo/a/aa060500a.html>.
"Cryogenics" *Science Clarified*, May 2, 2006 [retrieved from the internet on Aug. 17, 2012]. <URL: http://www.scienceclarified.com/Co-Di/Cryogenics.html>.
Denton, R. D. et al. (1985) "Integrated Low Temperature Processing of Sour Natural Gas," *Gas Processors Assoc., 64th Ann. Conv.*, pp. 92-96.
Guccione, E. (1963) "New Approach to Recovery of Helium from Natural Gas," *Chem. Engr.*, Sep. 30, 1963, pp. 76-78.

(56) References Cited

OTHER PUBLICATIONS

Hassan, S. M. N. (2005) "Techno-Economic Study of $CO_2$ Capture Process for Cement Plants," *University of Waterloo—Thesis*.

Haut, R. C. et al. (1988) "Development and Application of the Controlled Freeze Zone Process," *SPE 17757, SPE Gas Tech. Symp.—Dallas, TX*, pp. 435-443.

Haut, R. C. et al. (1988) "Development and Application of the Controlled Freeze Zone Process," *OSEA 88197, 7th Offshore So. East Asia Conf.*, Singapore, Feb. 1988, pp. 840-848.

Haut, R. C. et al. (1989) "Development and Application of the Controlled Freeze Zone Process," *SPE Production Engineering*, Aug. 1989, pp. 265-271.

Im, U. K. et al. (1971) "Heterogeneous Phase Behavior of Carbon Dioxide in n-Hexane and n-Heptane at Low Temperatures," *Jrnl. of Chem. Engineering Data*, v.16.4, pp. 412-415.

Mitariten, M. et al. (2007) "The Sorbead™ Quick-Cycle Process for Simultaneous Removal of Water, Heavy Hydrocarbons and Mercaptans from Natural Gas," *Laurance Reid Gas Conditioning Conf.*, Feb. 25-27, 2007.

Northrop, P. Scott et al. (2004) "Cryogenic Sour Gas Process Attractive for Acid Gas Injection Applications," *83rd Ann. Gas Processors Assoc. Convention*, New Orleans, LA., pp. 1-8 (XP007912217).

Pagcatipunan, C. et al. (2005) "Maximize the Performance of Spray Nozzle Systems," *CEP Magazine*, Dec. 2005, pp. 38-44.

Reyes, S. C. et al. (1997) "Frequency Modulation Methods for Diffusion and Adsorption Measurements in Porous Solids," *J. Phys. Chem. B*, v.101, pp. 614-622.

Rubin, E. S. et al. (2002) "A Technical, Economic and Environmental Assessment of Amine-based CO2 Capture Technology for Power Plant Greenhouse Gas Control," *U.S. Dept. of Energy*, Oct. 2002, DOE/DE-FC26-00NT40935, 26 pages.

Spero, C. (2007) "Callide Oxyfuel Project," *CS Energy, cLET Seminar*, Jul. 12, 2007, 9 pages.

Thomas, E. R. et al. (1987) "Conceptual Studies Using the Controlled Freeze Zone (CFZ) Process," *AlChE Summer Nat'l Mtg.*, Aug. 16-19, 1987.

Thomas, E. R. et al. (1988) "Conceptual Studies for $CO_2$/Natural Gas Separation Using the Control Freeze Zone (CFZ) Process," *Gas Separation and Purification*, v. 2, pp. 84-89.

Valencia, J. A. et al. (2008) "Controlled Freeze Zone™ Technology for Enabling Processing of High $CO_2$ and $H_2S$ Gas Reserves," SPE-IPTC 12708, Kuala Lumpur, IN, v.4.1, Jan. 2008, pp. 2358-2363.

Victory, D. J. et al. (1987) "The CFZ Process: Direct Methane-Carbon Dioxide Fractionation," *66th Ann. GPA Convention*, Mar. 16-18, Denver, CO.

Wilson, R.W. et al. (1968) "Helium: Its Extraction and Purification," *Journ. Petrol. Tech.*, v. 20, pp. 341-344.

\* cited by examiner

METHOD AND SYSTEM OF MAINTAINING A LIQUID LEVEL IN A DISTILLATION TOWER

CROSS REFERENCE TO RELATED APPLICATIONS

This application claims the priority benefit of U.S. Patent Application 61/912,959 filed Dec. 6, 2013 entitled METHOD AND SYSTEM OF MAINTAINING A LIQUID LEVEL IN A DISTILLATION TOWER, the entirety of which is incorporated by reference herein.

This application is related to but does not claim priority to U.S. Provisional patent application Nos. 61/912,957 filed on Dec. 6, 2013 entitled METHOD AND DEVICE FOR SEPARATING HYDROCARBONS AND CONTAMINANTS WITH A SPRAY ASSEMBLY; 62/044,770 filed on Sep. 2, 2014 entitled METHOD AND DEVICE FOR SEPARATING HYDROCARBONS AND CONTAMINANTS WITH A SPRAY ASSEMBLY; 61/912,964 filed on Dec. 6, 2013 entitled METHOD AND DEVICE FOR SEPARATING A FEED STREAM USING RADIATION DETECTORS; 61/912,970 filed on Dec. 6, 2013 entitled METHOD AND SYSTEM OF DEHYDRATING A FEED STREAM PROCESSED IN A DISTILLATION TOWER; 61/912,975 filed on Dec. 6, 2013 entitled METHOD AND SYSTEM FOR SEPARATING A FEED STREAM WITH A FEED STREAM DISTRIBUTION MECHANISM; 61/912,978 filed on Dec. 6, 2013 entitled METHOD AND SYSTEM FOR PREVENTING ACCUMULATION OF SOLIDS IN A DISTILLATION TOWER; 61/912,983 filed on Dec. 6, 2013 entitled METHOD OF REMOVING SOLDS BY MODIFYING A LIQUID LEVEL IN A DISTILLATION TOWER; 61/912,984 filed on Dec. 6, 2013 entitled METHOD AND SYSTEM OF MODIFYING A LIQUID LEVEL DURING START-UP OPERATIONS; 61/912,986 filed on Dec. 6, 2013 entitled METHOD AND DEVICE FOR SEPARATING HYDROCARBONS AND CONTAMINANTS WITH A HEATING MECHANISM TO DESTABILIZE AND/OR PREVENT ADHESION OF SOLIDS; 61/912,987 filed on Dec. 6, 2013 entitled METHOD AND DEVICE FOR SEPARATING HYDROCARBONS AND CONTAMINANTS WITH A SURFACE TREATMENT MECHANISM.

BACKGROUND

Fields of Disclosure

The disclosure relates generally to the field of fluid separation. More specifically, the disclosure relates to the cryogenic separation of contaminants, such as acid gas, from a hydrocarbon.

Description of Related Art

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as admissions of prior art.

The production of natural gas hydrocarbons, such as methane and ethane, from a reservoir oftentimes carries with it the incidental production of non-hydrocarbon gases. Such gases include contaminants, such as at least one of carbon dioxide ("$CO_2$"), hydrogen sulfide ("$H_2S$"), carbonyl sulfide, carbon disulfide and various mercaptans. When a feed stream being produced from a reservoir includes these contaminants mixed with hydrocarbons, the stream is oftentimes referred to as "sour gas."

Many natural gas reservoirs have relatively low percentages of hydrocarbons and relatively high percentages of contaminants. Contaminants may act as a diluent and lower the heat content of hydrocarbons. Some contaminants, like sulfur-bearing compounds, are noxious and may even be lethal. Additionally, in the presence of water some contaminants can become quite corrosive.

It is desirable to remove contaminants from a stream containing hydrocarbons to produce sweet and concentrated hydrocarbons. Specifications for pipeline quality natural gas typically call for a maximum of 2-4% $CO_2$ and ¼ grain $H_2S$ per 100 scf (4 ppmv) or 5 mg/Nm3 $H_2S$. Specifications for lower temperature processes such as natural gas liquefaction plants or nitrogen rejection units typically require less than 50 ppm $CO_2$.

The separation of contaminants from hydrocarbons is difficult and consequently significant work has been applied to the development of hydrocarbon/contaminant separation methods. These methods can be placed into three general classes: absorption by solvents (physical, chemical and hybrids), adsorption by solids, and distillation.

Separation by distillation of some mixtures can be relatively simple and, as such, is widely used in the natural gas industry. However, distillation of mixtures of natural gas hydrocarbons, primarily methane, and one of the most common contaminants in natural gas, carbon dioxide, can present significant difficulties. Conventional distillation principles and conventional distillation equipment are predicated on the presence of only vapor and liquid phases throughout the distillation tower. The separation of $CO_2$ from methane by distillation involves temperature and pressure conditions that result in solidification of $CO_2$ if a pipeline or better quality hydrocarbon product is desired. The required temperatures are cold temperatures typically referred to as cryogenic temperatures.

Certain cryogenic distillations can overcome the above mentioned difficulties. These cryogenic distillations provide the appropriate mechanism to handle the formation and subsequent melting of solids during the separation of solid-forming contaminants from hydrocarbons. The formation of solid contaminants in equilibrium with vapor-liquid mixtures of hydrocarbons and contaminants at particular conditions of temperature and pressure takes place in a controlled freeze zone section.

The solid contaminants formed in the controlled freeze zone section fall into a liquid of the controlled freeze zone section that is held above the melting point of the solid contaminants. The liquid is held at a sufficiently warm temperature to melt the solid contaminants. The liquid is part of a melt tray assembly of the controlled freeze zone section. To ensure that all of the solid contaminants melt in the liquid and none exit the controlled freeze zone section and/or plug a liquid discharge line, there needs to be sufficient warm liquid thermal mass in the controlled freeze zone section. In other words, the liquid in the melt tray assembly needs to at least be at a predetermined liquid level.

Liquid level indicators, such as differential pressure cells, guided wave radar sensors and a nucleonic mechanism have been used to help determine the liquid level, but these indicators have disadvantages. Differential pressure cells do not work well in determining the liquid level if the solid contaminants plug the differential pressure cells or associated pressure taps. Guided wave radar sensors do not work well because the temperature and pressure of the controlled freeze zone section is too close to the critical conditions of liquid and vapor, thereby making liquid and vapor nearly indistinguishable. Furthermore, compositional and pressure changes of the stream can cause changes in fluid density, making measurements inconsistent over time. The nucleonic mechanism does not work well in the presence of unsteady amounts of solids.

A need exists for improved technology that maintains at least a predetermined liquid level in a distillation tower so that a minimum warm liquid thermal mass is provided to reliably melt all solid contaminants in the liquid of the melt tray assembly and so that plugging of the controlled freeze zone section liquid discharge is avoided.

SUMMARY

The present disclosure provides a device and method for separating contaminants from hydrocarbons, among other things.

A distillation tower may comprise a stripper section constructed and arranged to separate a feed stream at a temperature and pressure at which the feed stream forms no solid; a controlled freeze zone section constructed and arranged to separate the feed stream at a temperature and pressure at which the feed stream forms a solid; a melt tray assembly in the controlled freeze zone section that includes a liquid; an underflow weir in the controlled freeze zone section that alters a flow of the liquid in the melt tray assembly; an overflow weir in the controlled freeze zone section that works with the underflow weir to alter the flow of the liquid in the melt tray assembly and is adjacent to the underflow weir; and a covering element in the controlled freeze zone section that is connected to and extends from the underflow weir.

A method of maintaining a liquid level in a distillation tower may comprise forming a freezing zone vapor stream from a feed stream in a stripper section of a distillation tower at a temperature and pressure at which no solid forms in the stripper section; forming a solid in a controlled freeze zone section of the distillation tower from the feed stream; and maintaining a predetermined liquid level of liquid in a melt tray assembly of the controlled freeze zone section by: altering a flow of the liquid in the melt tray assembly such that the liquid flows from a bottom melt tray assembly portion of the melt tray assembly to a top melt tray assembly portion of the melt tray assembly; and altering the flow of the liquid in the melt tray assembly such that the liquid flows from the top melt tray assembly portion toward the stripper section.

A method for producing hydrocarbons may comprise forming a freezing zone vapor stream from a feed stream in a stripper section of a distillation tower at a temperature and pressure at which no solid forms in the stripper section; forming a solid in a controlled freeze zone section of the distillation tower from the feed stream; maintaining a predetermined liquid level of liquid in a melt tray assembly of the controlled freeze zone section by: altering a flow of the liquid in the melt tray assembly such that the liquid flows from a bottom melt tray assembly portion of the melt tray assembly to a top melt tray assembly portion of the melt tray assembly; and altering the flow of the liquid in the melt tray assembly such that the liquid flows from the top melt tray assembly portion toward the stripper section; and producing hydrocarbons from the feed stream.

The foregoing has broadly outlined the features of the present disclosure in order that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

For the purpose of promoting an understanding of the principles of the disclosure, reference will now be made to the features illustrated in the drawings and specific language will be used to describe the same. It will nevertheless be understood that no limitation of the scope of the disclosure is thereby intended. Any alterations and further modifications, and any further applications of the principles of the disclosure as described herein are contemplated as would normally occur to one skilled in the art to which the disclosure relates. It will be apparent to those skilled in the relevant art that some features that are not relevant to the present disclosure may not be shown in the drawings for the sake of clarity.

As referenced in this application, the terms "stream," "gas stream," "vapor stream," and "liquid stream" refer to different stages of a feed stream as the feed stream is processed in a distillation tower that separates methane, the primary hydrocarbon in natural gas, from contaminants. Although the phrases "gas stream," "vapor stream," and "liquid stream," refer to situations where a gas, vapor, and liquid is mainly present in the stream, respectively, there may be other phases also present within the stream. For example, a gas may also be present in a "liquid stream." In some instances, the terms "gas stream" and "vapor stream" may be used interchangeably.

The disclosure relates to a system and method for separating a feed stream in a distillation tower. The system and method maintains a predetermined liquid level in the controlled freeze zone section. FIGS. 1-7 of the disclosure display various aspects of the system and method.

Figure 1:
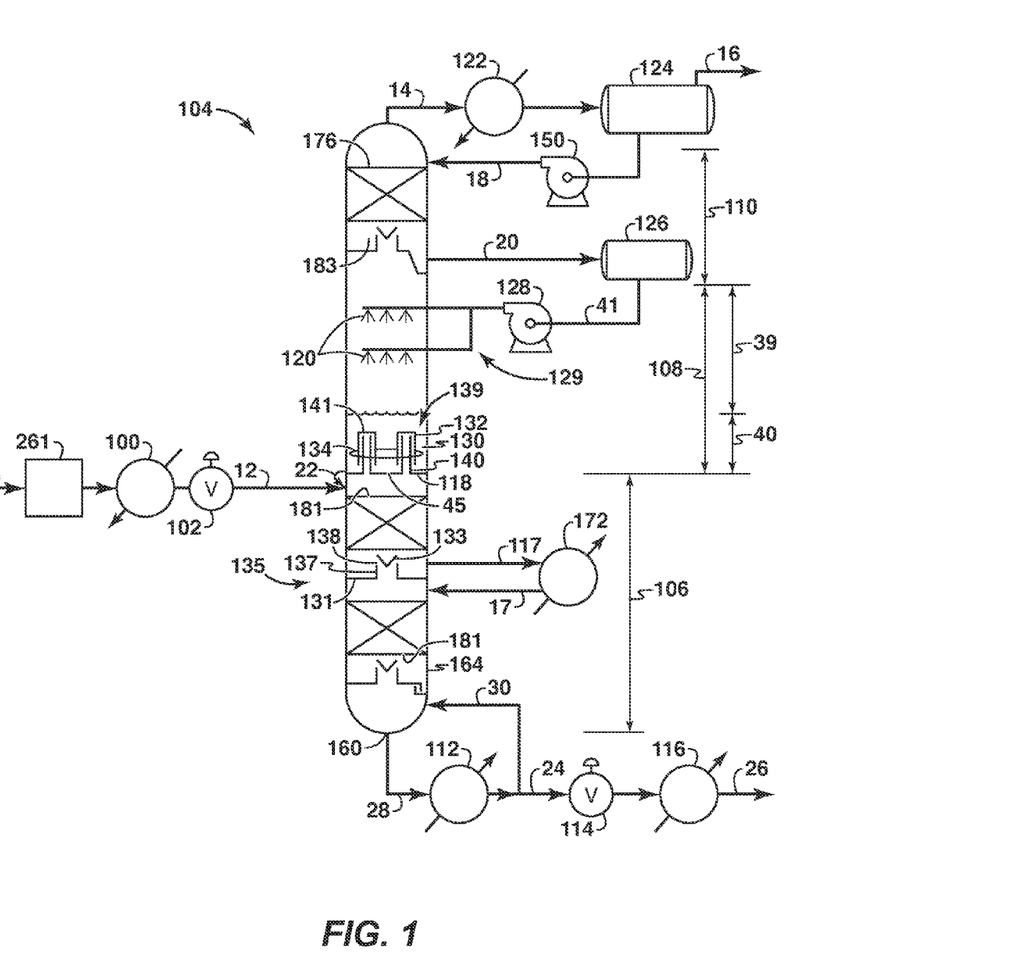
FIG. 1 is a schematic diagram of a tower with sections within a single vessel.
Figure 2:
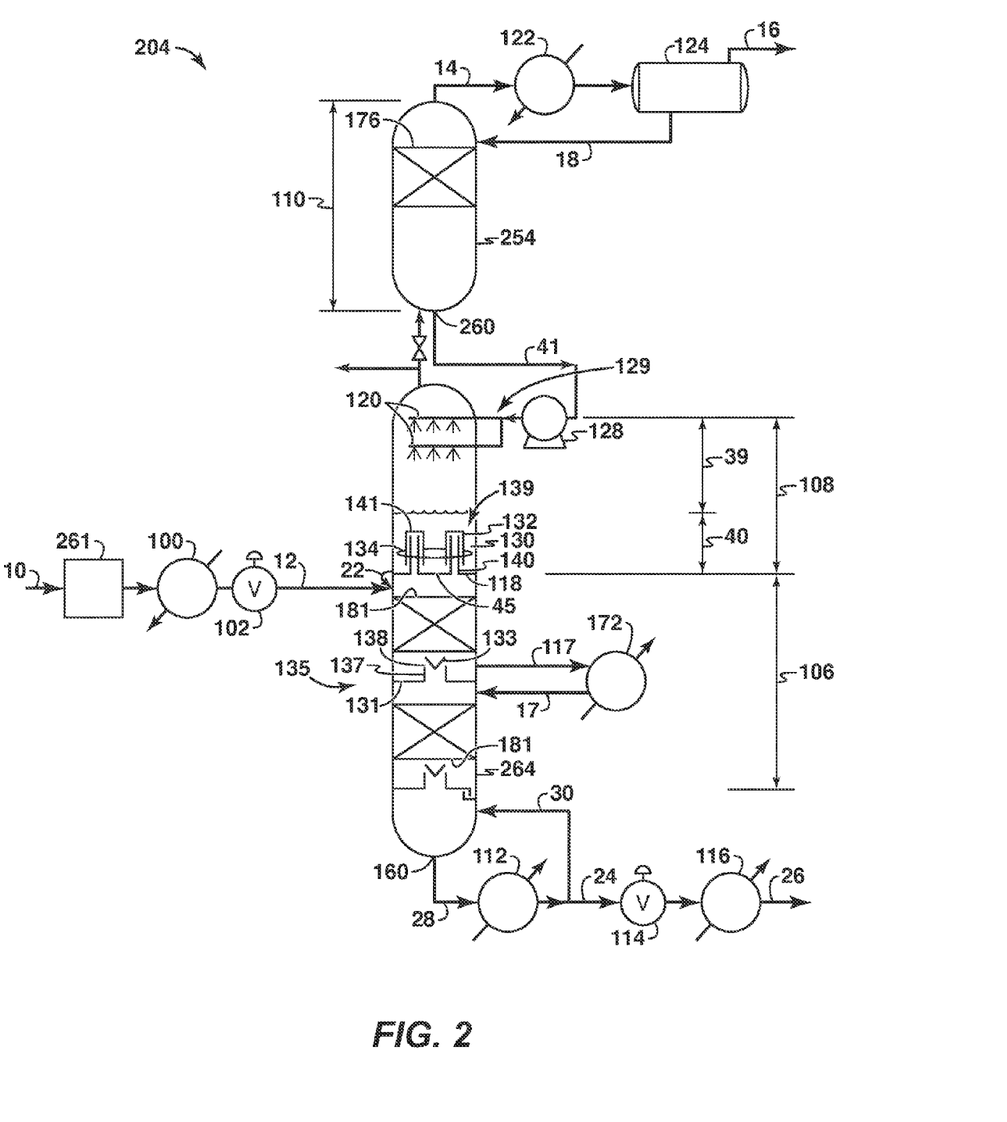
FIG. 2 is a schematic diagram of a tower with sections within multiple vessels.

The system and method may separate a feed stream having methane and contaminants. The system may comprise a distillation tower 104, 204 (FIGS. 1-2). The distillation tower 104, 204 may separate the contaminants from the methane.

The distillation tower 104, 204 may be separated into three functional sections: a lower section 106, a middle controlled freeze zone section 108 and an upper section 110.

The distillation tower 104, 204 may incorporate three functional sections when the upper section 110 is needed and/or desired.

The distillation tower 104, 204 may incorporate only two functional sections when the upper section 110 is not needed and/or desired. When the distillation tower does not include an upper section 110, a portion of vapor leaving the middle controlled freeze zone section 108 may be condensed in a condenser 122 and returned as a liquid stream via a spray assembly 129. Moreover, lines 18 and 20 may be eliminated, elements 124 and 126 may be one and the same, and elements 150 and 128 may be one and the same. The stream in line 14, now taking the vapors leaving the middle controlled freeze section 108, directs these vapors to the condenser 122.

The lower section 106 may also be referred to as a stripper section. The middle controlled section 108 may also be referred to as the controlled freeze zone section. The upper section 110 may also be referred to as a rectifier section.

Figure 3:
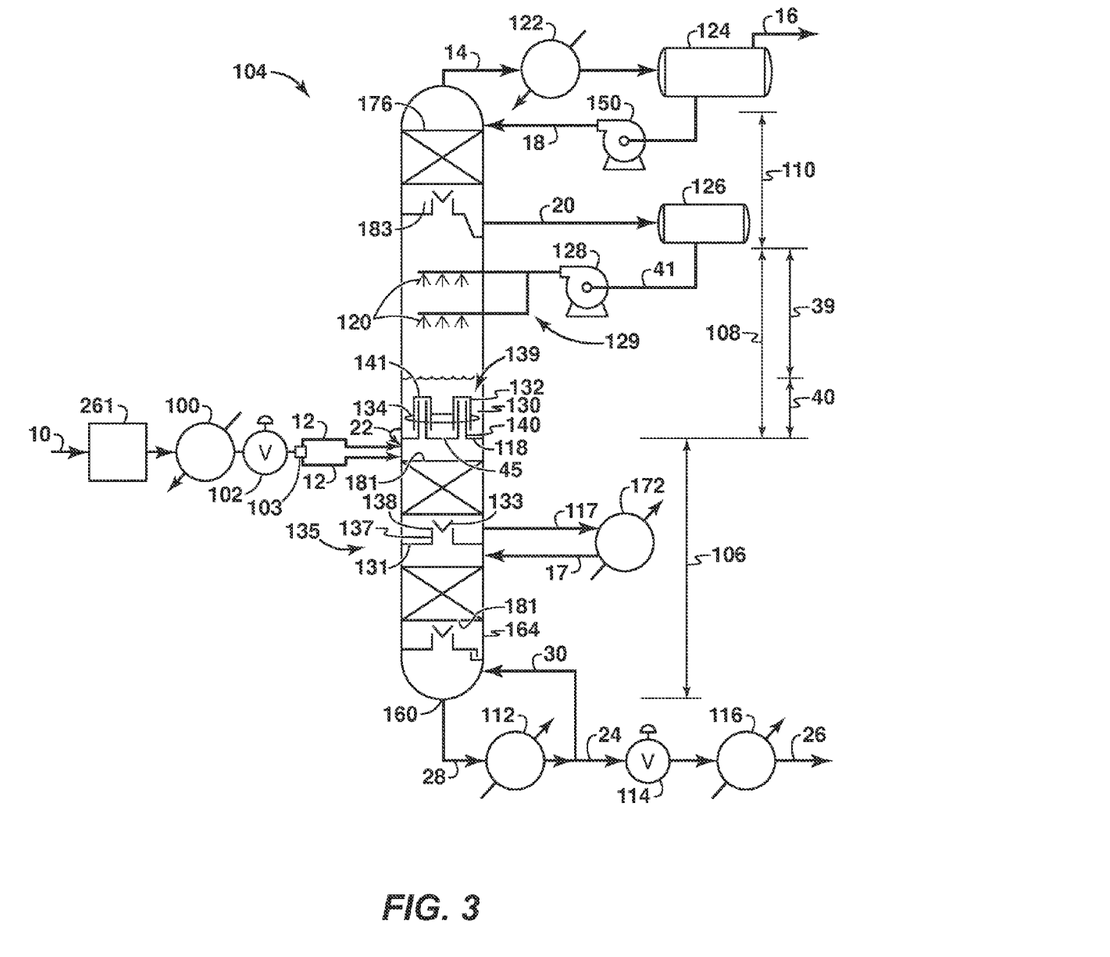
FIG. 3 is a schematic diagram of a tower with sections within a single vessel.

The sections of the distillation tower 104 may be housed within a single vessel (FIGS. 1 and 3). For example, the lower section 106, the middle controlled freeze zone section 108, and the upper section 110 may be housed within a single vessel 164.

Figure 4:
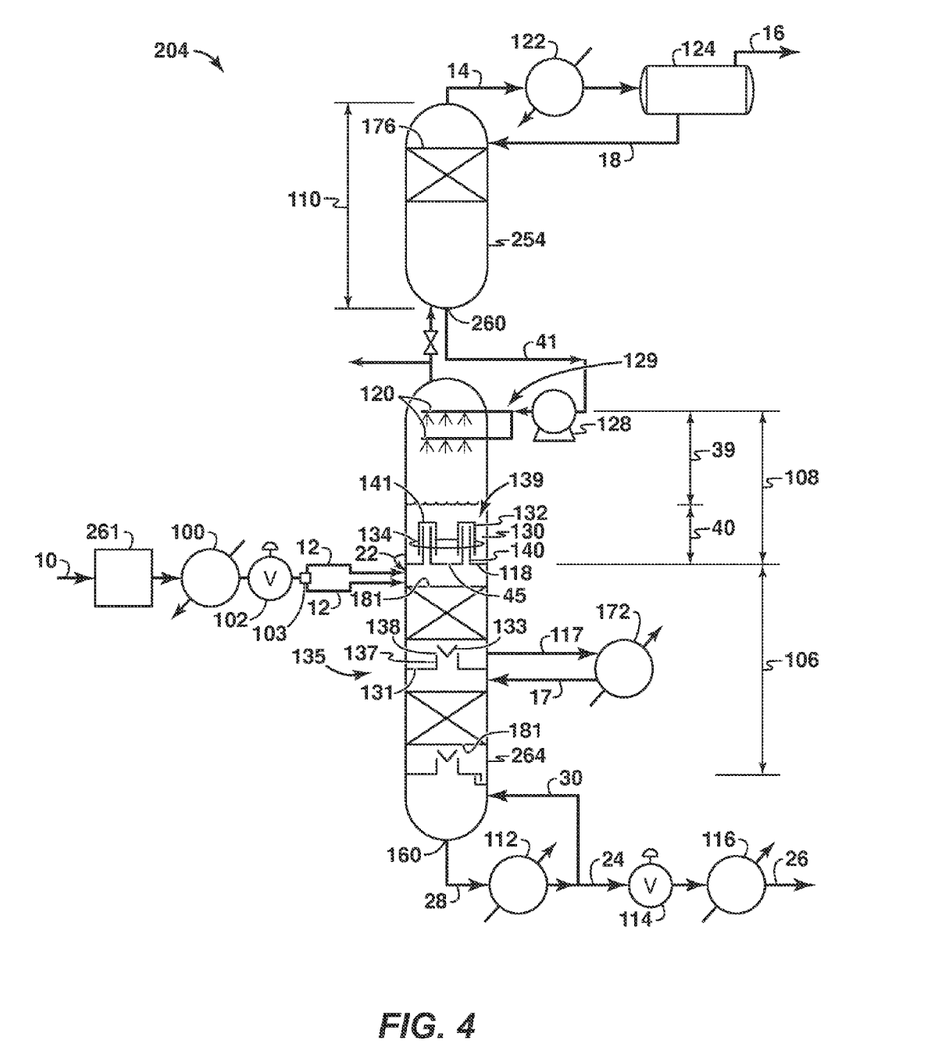
FIG. 4 is a schematic diagram of a tower with sections within multiple vessels.

The sections of the distillation tower 204 may be housed within a plurality of vessels to form a split-tower configuration (FIGS. 2 and 4). Each of the vessels may be separate from the other vessels. Piping and/or another suitable mechanism may connect one vessel to another vessel. In this instance, the lower section 106, middle controlled freeze zone section 108 and upper section 110 may be housed within two or more vessels. For example, as shown in FIGS. 2 and 4, the upper section 110 may be housed within a single vessel 254 and the lower and middle controlled freeze zone sections 106, 108 may be housed within a single vessel 264. When this is the case, a liquid stream exiting the upper section 110, may exit through a liquid outlet bottom 260. The liquid outlet bottom 260 is at the bottom of the upper section 110. Although not shown, each of the sections may be housed within its own separate vessel, or one or more section may be housed within separate vessels, or the upper and middle controlled freeze zone sections may be housed within a single vessel and the lower section may be housed within a single vessel, etc. When sections of the distillation tower are housed within vessels, the vessels may be side-by-side along a horizontal line and/or above each other along a vertical line.

The split-tower configuration may be beneficial in situations where the height of the distillation tower, motion considerations, and/or transportation issues, such as for remote locations, need to be considered. This split-tower configuration allows for the independent operation of one or more sections. For example, when the upper section is housed within a single vessel and the lower and middle controlled freeze zone sections are housed within a single vessel, independent generation of reflux liquids using a substantially contaminant-free, largely hydrocarbon stream from a packed gas pipeline or an adjacent hydrocarbon line, may occur in the upper section. And the reflux may be used to cool the upper section, establish an appropriate temperature profile in the upper section, and/or build up liquid inventory at the bottom of the upper section to serve as an initial source of spray liquids for the middle controlled freeze zone section. Moreover, the middle controlled freeze zone and lower sections may be independently prepared by chilling the feed stream, feeding it to the optimal location be that in the lower section or in the middle controlled freeze zone section, generating liquids for the lower and the middle controlled freeze zone sections, and/or disposing the vapors off the middle controlled freeze zone section while they are off specification with too high a contaminant content. Also, liquid from the upper section may be intermittently or continuously sprayed, building up liquid level in the bottom of the middle controlled freeze zone section and bringing the contaminant content in the middle controlled freeze zone section down and near steady state level so that the two vessels may be connected to send the vapor stream from the middle controlled freeze zone section to the upper section, continuously spraying liquid from the bottom of the upper section into the middle controlled freeze zone section and stabilizing operations into steady state conditions. The split tower configuration may utilize a sump of the upper section as a liquid receiver for the pump 128, therefore obviating the need for a liquid receiver 126 in FIGS. 1 and 3.

The system may also include a heat exchanger 100 (FIGS. 1-4). The feed stream 10 may enter the heat exchanger 100 before entering the distillation tower 104, 204. The feed stream 10 may be cooled within the heat exchanger 100. The heat exchanger 100 helps drop the temperature of the feed stream 10 to a level suitable for introduction into the distillation tower 104, 204.

The system may include an expander device 102 (FIGS. 1-4). The feed stream 10 may enter the expander device 102 before entering the distillation tower 104, 204. The feed stream 10 may be expanded in the expander device 102 after exiting the heat exchanger 100. The expander device 102 helps drop the temperature of the feed stream 10 to a level suitable for introduction into the distillation tower 104, 204. The expander device 102 may be any suitable device, such as a valve. If the expander device 102 is a valve, the valve may be any suitable valve that may aid in cooling the feed stream 10 before it enters the distillation tower 104, 204. For example, the valve 102 may comprise a Joule-Thompson (J-T) valve.

The system may include a feed separator 103 (FIGS. 3-4). The feed stream may enter the feed separator before entering the distillation tower 104, 204. The feed separator may separate a feed stream having a mixed liquid and vapor stream into a liquid stream and a vapor stream. Lines 12 may extend from the feed separator to the distillation tower 104, 204. One of the lines 12 may receive the vapor stream from the feed separator. Another one of the lines 12 may receive the liquid stream from the feed separator. Each of the lines 12 may extend to the same and/or different sections (i.e. middle controlled freeze zone, and lower sections) of the distillation tower 104, 204. The expander device 102 may or may not be downstream of the feed separator 103. The expander device 102 may comprise a plurality of expander devices 102 such that each line 12 has an expander device 102.

The system may include a dehydration unit 261 (FIGS. 1-4). The feed stream 10 may enter the dehydration unit 261 before entering the distillation tower 104, 204. The feed stream 10 enters the dehydration unit 261 before entering the heat exchanger 100 and/or the expander device 102. The dehydration unit 261 removes water from the feed stream 10 to prevent water from later presenting a problem in the heat exchanger 100, expander device 102, feed separator 103, or distillation tower 104, 204. The water can present a problem by forming a separate water phase (i.e., ice and/or hydrate) that plugs lines, equipment or negatively affects the distillation process. The dehydration unit 261 dehydrates the feed stream to a dew point sufficiently low to ensure a separate water phase does not form at any point downstream during the rest of the process. The dehydration unit may be any suitable dehydration mechanism, such as a molecular sieve or a glycol dehydration unit.

The system may include a filtering unit (not shown). The feed stream 10 may enter the filtering unit before entering the distillation tower 104, 204. The filtering unit may remove undesirable contaminants from the feed stream before the feed stream enters the distillation tower 104, 204. Depending on what contaminants are to be removed, the filtering unit may be before or after the dehydration unit 261 and/or before or after the heat exchanger 100.

The system may include a line 12 (FIGS. 1-4). The line may also be referred to as an inlet channel 12. The feed stream 10 may be introduced into the distillation tower 104, 204 through the line 12. The line 12 may extend to the lower section 106 or the middle controlled freeze zone section 108 of the distillation tower 104, 204. For example, the line 12 may extend to the lower section 106 such that the feed stream 10 may enter the lower section 106 of the distillation tower 104, 204 (FIGS. 1-4). The line 12 may directly or indirectly extend to the lower section 106 or the middle controlled freeze zone section 108. The line 12 may extend to an outer surface of the distillation tower 104, 204 before entering the distillation tower.

If the system includes the feed separator 103 (FIGS. 3-4), the line 12 may comprise a plurality of lines 12. Each line may be the same line as one of the lines that extends from the feed separator to a specific portion of the distillation tower 104, 204.

The lower section 106 is constructed and arranged to separate the feed stream 10 into an enriched contaminant bottom liquid stream (i.e., liquid stream) and a freezing zone vapor stream (i.e., vapor stream), 301. The lower section 106 separates the feed stream at a temperature, pressure, and/or composition at which no solids form. The liquid stream may comprise a greater quantity of contaminants than of methane. The vapor stream may comprise a greater quantity of methane than of contaminants. In any case, the vapor stream is lighter than the liquid stream. As a result, the vapor stream rises from the lower section 106 and the liquid stream falls to the bottom of the lower section 106.

The lower section 106 may include and/or connect to equipment that separates the feed stream. The equipment may comprise any suitable equipment for separating methane from contaminants, such as one or more packed sections 181, or one or more distillation trays with perforations, downcomers and weirs (FIGS. 1-4).

The equipment may include components that apply heat to the stream to form the vapor stream and the liquid stream. For example, the equipment may comprise a first reboiler 112 that applies heat to the stream. The first reboiler 112 may be located outside of the distillation tower 104, 204. The equipment may also comprise a second reboiler 172 that applies heat to the stream. The second reboiler 172 may be located outside of the distillation tower 104, 204. Line 117 may lead from the distillation tower to the second reboiler 172. Line 17 may lead from the second reboiler 172 to the distillation tower. Additional reboilers, set up similarly to the second reboiler described above, may also be used.

The first reboiler 112 may apply heat to the liquid stream that exits the lower section 106 through a liquid outlet 160 of the lower section 106. The liquid stream may travel from the liquid outlet 160 through line 28 to reach the first reboiler 112 (FIGS. 1-4). The amount of heat applied to the liquid stream by the first reboiler 112 can be increased to separate more methane from contaminants. The more heat applied by the reboiler 112 to the stream, the more methane separated from the liquid contaminants, though more contaminants will also be vaporized.

The first reboiler 112 may also apply heat to the stream within the distillation tower 104, 204. Specifically, the heat applied by the first reboiler 112 warms up the lower section 106. This heat travels up the lower section 106 and supplies heat to warm solids entering a melt tray assembly 139 (FIGS. 1-2) of the middle controlled freeze zone section 108 so that the solids form a liquids and/or slurry mix.

The second reboiler 172 applies heat to the stream within the lower section 106. This heat is applied closer to the middle controlled freeze zone section 108 than the heat applied by the first reboiler 112. As a result, the heat applied by the second reboiler 172 reaches the middle controlled freeze zone section 108 faster than the heat applied by the first reboiler 112. The second reboiler 172 also helps with energy integration.

The equipment may include one or more chimney assemblies 135 (FIGS. 1-4). While falling to the bottom of the lower section 106, the liquid stream may encounter one or more of the chimney assemblies 135.

Each chimney assembly 135 includes a chimney tray 131 that collects the liquid stream within the lower section 106. The liquid stream that collects on the chimney tray 131 may be fed to the second reboiler 172. After the liquid stream is heated in the second reboiler 172, the stream may return to the middle controlled freeze zone section 106 to supply heat to the middle controlled freeze zone section 106 and/or the melt tray assembly 139. Unvaporized stream exiting the second reboiler 172 may be fed back to the distillation tower 104, 204 below the chimney tray 131. Vapor stream exiting the second reboiler 172 may be routed under or above the chimney tray 131 when the vapor stream enters the distillation tower 104, 204.

The chimney tray 131 may include one or more chimneys 137. The chimney 137 serves as a channel that the vapor stream in the lower section 106 traverses. The vapor stream travels through an opening in the chimney tray 131 at the bottom of the chimney 137 to the top of the chimney 137. The opening is closer to the bottom of the lower section 106 than it is to the bottom of the middle controlled freeze zone section 108. The top is closer to the bottom of the middle controlled freeze zone section 108 than it is to the bottom of the lower section 106.

Each chimney 137 has attached to it a chimney cap 133. The chimney cap 133 covers a chimney top opening 138 of the chimney 137. The chimney cap 133 prevents the liquid stream from entering the chimney 137. The vapor stream exits the chimney assembly 135 via the chimney top opening 138.

After falling to the bottom of the lower section 106, the liquid stream exits the distillation tower 104, 204 through the liquid outlet 160. The liquid outlet 160 is within the lower section 106 (FIGS. 1-4). The liquid outlet 160 may be located at the bottom of the lower section 106.

After exiting through the liquid outlet 160, the feed stream may travel via line 28 to the first reboiler 112. The feed stream may be heated by the first reboiler 112 and vapor may then re-enter the lower section 106 through line 30. Unvaporized liquid may continue out of the distillation process via line 24.

The system may include an expander device 114 (FIGS. 1-4). After entering line 24, the heated liquid stream may be expanded in the expander device 114. The expander device 114 may be any suitable device, such as a valve. The valve 114 may be any suitable valve, such as a J-T valve.

The system may include a heat exchanger 116 (FIGS. 1-4). The liquid stream heated by the first reboiler 112 may be cooled or heated by the heat exchanger 116. The heat exchanger 116 may be a direct heat exchanger or an indirect heat exchanger. The heat exchanger 116 may comprise any suitable heat exchanger.

Figure 7:
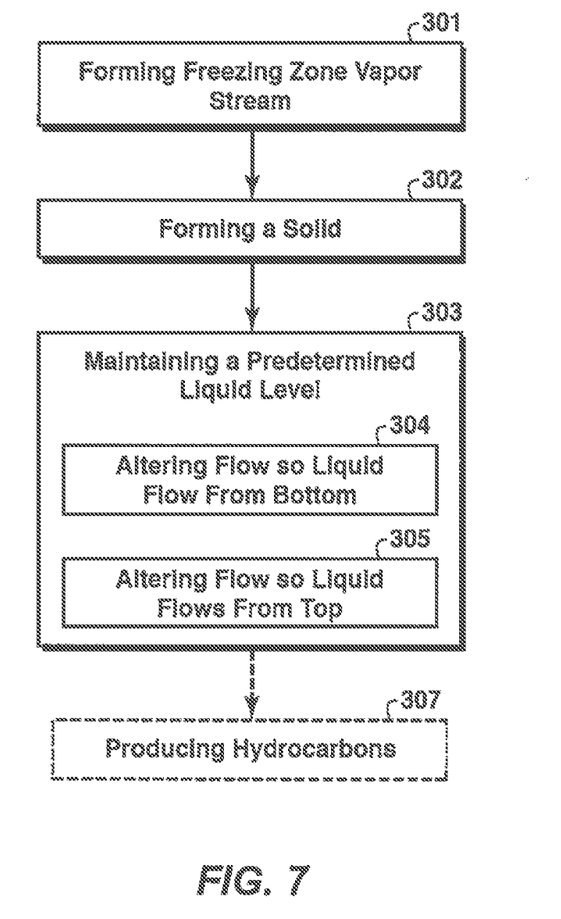
FIG. 7 is a flowchart of a method within the scope of the present disclosure.

The vapor stream in the lower section 106 rises from the lower section 106 to the middle controlled freeze zone section 108. The middle controlled freeze zone section 108 is constructed and arranged to separate the feed stream 10 introduced into the middle controlled freeze zone section, or into the top of lower section 106, into a solid and a vapor stream. The solid may be comprised more of contaminants than of methane. The vapor stream (i.e., methane-enriched vapor stream) may comprise more methane than contaminants. The middle controlled freeze zone section 108 operates at least one of a temperature, pressure and composition at which the feed stream forms the solid and the vapor stream 302 (FIG. 7).

Figure 5:
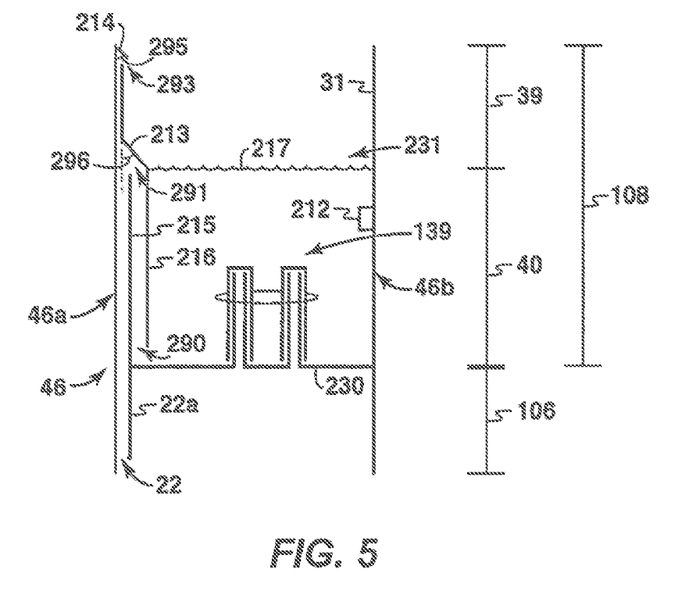
FIG. 5 is a schematic diagram of a portion of a distillation tower.

The middle controlled freeze zone section 108 includes a lower section 40 and an upper section 39 (FIG. 5). The lower section 40 is below the upper section 39. The lower section 40 directly abuts the upper section 39. The lower section 40 is primarily but not exclusively a heating section of the middle controlled freeze zone section 108. The upper section 39 is primarily but not exclusively a cooling section of the middle controlled freeze zone section 108. At least one of the temperature, pressure, and/or composition of the upper section 39 is chosen so that the solid can form in the middle controlled freeze zone section 108.

The middle controlled freeze zone section 108 may comprise a melt tray assembly 139 that is maintained in the middle controlled freeze zone section 108 (FIGS. 1-5). The melt tray assembly 139 is within the lower section 40 of the middle controlled freeze section 108. The melt tray assembly 139 is not within the upper section 39 of the middle controlled freeze zone section 108.

The melt tray assembly 139 is constructed and arranged to melt solids formed in the middle controlled freeze zone section 108. When the warm vapor stream rises from the lower section 106 to the middle controlled freeze zone section 108, the vapor stream immediately encounters the melt tray assembly 139 and supplies heat to melt the solids. The melt tray assembly 139 may comprise at least one of a melt tray 118, a bubble cap 132, a liquid 130 and heat mechanism(s) 134.

The melt tray 118 may collect a liquid and/or slurry mix. The melt tray 118 divides at least a portion of the middle controlled freeze zone section 108 from the lower section 106. Consequently, the melt tray 118 is at the bottom 45 of the middle controlled freeze zone section 108.

One or more bubble caps 132 may act as a channel for the vapor stream rising from the lower section 106 to the middle controlled freeze zone section 108. The bubble cap 132 may provide a path for the vapor stream up the riser 140 and then down and around the riser 140 to the melt tray 118. The riser 140 is covered by a cap 141. The cap 141 prevents the liquid 130 from travelling into the riser and it also helps prevent solids from travelling into the riser 140. The vapor stream's traversal through the bubble cap 132 allows the vapor stream to transfer heat to the liquid 130 within the melt tray assembly 139.

One or more heat mechanisms 134 may further heat up the liquid 130 to facilitate melting of the solids into a liquid and/or slurry mix. The heat mechanism(s) 134 may be located anywhere within the melt tray assembly 139. For example, as shown in FIGS. 1-4, a heat mechanism 134 may be located around bubble caps 132. The heat mechanism 134 may be any suitable mechanism, such as a heat coil. The heat source of the heat mechanism 134 may be any suitable heat source.

The liquid 130 in the melt tray assembly is heated by the vapor stream. The liquid 130 may also be heated by the one or more heat mechanisms 134. The liquid 130 helps melt the solids formed in the middle controlled freeze zone section 108 into a liquid and/or slurry mix. Specifically, the heat transferred by the vapor stream heats up the liquid, thereby enabling the heat to melt the solids.

The liquid 130 accumulates in the melt tray assembly 139. The liquid 130 rises to reach a certain liquid level 217. For all of the solids to melt, the liquid level 217 needs to at least be equal to a predetermined liquid level. The predetermined liquid level is one that provides a sufficient warm thermal mass to reliably melt all solids. When the liquid level is at least at this predetermined liquid level, it is more likely that the middle controlled freeze zone section 108 will operate properly by forming solids and vapors and melting the solids in the melt tray assembly 139, such that the methane in the feed stream is separated out from the contaminants in the feed stream.

Figure 6:
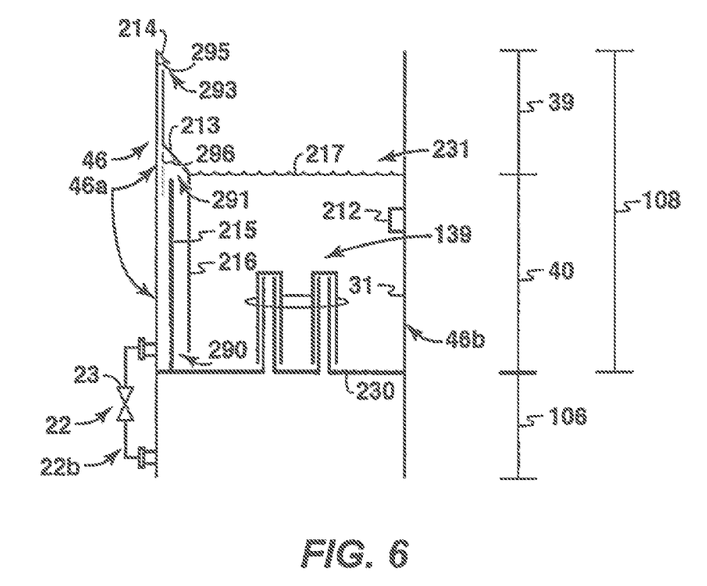
FIG. 6 is a schematic diagram of a portion of a distillation tower.

The middle controlled freeze zone section 108 may also comprise an underflow weir 216 and an overflow weir 215 (FIGS. 5-6). The underflow weir 216 and the overflow weir 215 work together to alter the flow of the liquid in the melt tray assembly 139 to help the liquid at least be at the predetermined liquid level 303 (FIG. 7). The overflow weir 215 may be directly adjacent to the underflow weir 216. The overflow weir 215 may also be directly adjacent to the controlled freeze zone wall 46 of the middle controlled freeze zone section 108.

Without both an overflow weir 215 and an underflow weir 216, solids and/or colder liquid may fall from the middle controlled freeze zone section 108 to the lower section 106, thereby preventing adequate separation of the feed stream. The solids may fall, for example, if the middle controlled freeze zone section 108 only includes an overflow weir 215 because solids may fall between the overflow weir 215 and a controlled freeze zone wall 46 of the middle controlled freeze zone section 108. The colder liquid may fall, for example, because the colder liquid is at the top of the melt tray assembly 139 and, therefore, the most likely to travel over the overflow weir 216 and down to the bottom distillation section 106. The warmer liquid, which is what is most desired to fall to the bottom distillation section 106, is at the bottom of the melt tray assembly 139.

With both the overflow weir 215 and the underflow weir 216, the warmer liquid at the bottom of the melt tray assembly 139 flows to the bottom distillation section 106. The underflow weir 216 alters the flow of the liquid such that the liquid flows from a melt tray assembly bottom portion 230 of the melt tray assembly 139 to a melt tray assembly top portion 231 of the melt tray assembly 139, 304 (FIG. 7). When the liquid flows from the melt tray assembly bottom portion 230, the liquid flows through an underflow gap 290 (FIGS. 5-6) of the underflow weir 216 to in between the underflow weir 216 and the overflow weir 215 and then to the melt tray assembly top portion 231. From there the overflow weir 215 alters the flow of the liquid such that the liquid flows from the melt tray assembly top portion 231 toward the lower section 106, 305 (FIG. 7). When the liquid flows from the melt tray assembly top portion 231, the liquid travels through an overflow gap 291 (FIGS. 5-6) of the overflow weir 215 and then travels between the overflow weir 215 and the controlled freeze zone wall 46 toward the lower section 106.

When the warmer liquid travels between the overflow weir 215 and the controlled freeze zone wall 46 the warmer liquid may directly or indirectly travel from the middle controlled freeze zone section 108 to the lower section 106. A channel 22 (FIGS. 5-6) may connect the middle controlled freeze zone section 108 to the lower section 106.

The channel 22 may comprise an internal channel 22a (FIG. 5). The internal channel 22a is inside of the middle controlled freeze zone section 108 and the lower section 106 (FIG. 5). The internal channel 22a includes the overflow weir 215. The internal channel 22a separates the controlled freeze zone wall 46 from the overflow weir 215. The internal channel 22a may or may not include a flow control device. When the internal channel 22a includes a flow control device (not shown), the maximum liquid level of the liquid 130 can fluctuate. The flow control device regulates the amount of liquid that flows from the middle controlled freeze zone section 108 to the lower section 106. For example, when the flow control device is fully open, the maximum liquid level is the predetermined liquid level set by the overflow weir 215 and when the flow control device is fully closed the maximum liquid level is greater than the predetermined liquid level. The higher liquid level allowed by the partially or fully closed flow control device allows for the liquid to melt solids that may accumulate above the predetermined liquid level if the liquid remains at the higher level for a sufficient period of time. A sufficient period of time may be, for example, from 5 to 30 minutes. The flow control device may be any suitable device, such as a sliding port or a control valve. When the internal channel 22a does not include a flow control device (FIG. 5), the maximum liquid level is the predetermined liquid level.

The channel 22 may comprise an external channel 22b. The external channel 22b is outside of the middle controlled freeze zone section 108 and the lower section 106 (FIG. 6). The external channel 22b is not within the distillation tower 104, 204. The external channel 22b may or may not include a flow control device. When the external channel 22b includes a flow control device 23 (FIG. 6), the maximum liquid level of the liquid 130 can fluctuate. The flow control device 23 regulates the amount of liquid that flows from the middle controlled freeze zone section 108 to the lower section 106. For example, when the flow control device is fully open, the maximum liquid level is the predetermined liquid level set by the overflow weir 215 and when the flow control device is fully closed the maximum liquid level is greater than the predetermined liquid level. The higher liquid level allowed by the partially or fully closed flow control device 23 allows for the liquid to melt solids that may accumulate above the predetermined liquid level if the liquid remains at the higher level for a sufficient period of time. A sufficient period of time may be, for example, from 5 to 30 minutes. The flow control device 23 may be any suitable device, such as a control valve or a sliding port. When the external channel 22b does not include a flow control device (not shown), the maximum liquid level is the predetermined liquid level.

While the above two paragraphs discuss the channel 22 comprising an internal channel 22a or an external channel 22b, the channel 22 could comprise an internal channel 22a and an external channel 22b.

To prevent solids from falling between the overflow weir 215 and the controlled freeze zone wall 46 and undesirably exiting to the lower section 106, the middle controlled freeze zone section 108 may include a covering element 213 (FIGS. 5-6). The covering element 213 may also help prevent accumulation of solid in the middle controlled freeze zone section 108 by having a suitably steep angle 296. The angle 296 may be any angle within and including the range of 1 to 45 degrees relative to the controlled freeze zone wall 46. The covering element 213 is connected to and extends from the underflow weir 216. The covering element 213 extends from the underflow weir 216 toward the controlled freeze zone wall 46 (FIGS. 5-6). The covering element 213 may be detached from the controlled freeze zone wall 46 (FIGS. 5-6). The covering element 213 may extend toward the overflow weir 215 from the underflow weir 216 and over the overflow weir 215. The covering element 213 may be detached from the overflow weir 215. Because the covering element 213 extends from the underflow weir 216 toward the controlled freeze zone wall 46, solids that could otherwise fall between the underflow weir 215, the overflow weir 216 and/or the controlled freeze zone wall 46 if there was no covering element 213, are prevented from falling between the overflow weir 215 and the controlled freeze zone wall 46. Additionally or alternatively, solids may also be prevented from falling between the overflow weir 215 and the underflow weir 216.

Vapor may accumulate in the space between the controlled freeze zone wall 46 and the overflow weir 215 when the warm liquid reaches this space. To prevent accumulation of the vapor in the middle controlled freeze zone section 108 while altering the flow of the liquid, the middle controlled freeze zone section 108 may include an anti-vapor lock 214. If the vapor accumulates, it may be stuck between the controlled freeze zone wall 46 and the overflow weir 215 without an anti-vapor lock. The anti-vapor lock may extend from the controlled freeze zone wall 46 to the covering element 213.

The anti-vapor lock 214 may extend from the controlled freeze zone wall 46 to the covering element 213 at an acute angle to the controlled freeze zone wall 46. The anti-vapor lock 214 may be at a suitable angle 295 (FIGS. 5-6) to prevent solids accumulations. For example, the anti-vapor lock 214 may be any angle 295 including and within the range of 1 to 45 degrees relative to the controlled freeze zone wall 46.

There is a gap 293 (FIGS. 5-6) between the end of the anti-vapor lock 214 that is closest to an end of the covering element 213. The gap 293 between the end of the covering element 213 and the anti-vapor lock 214 can provide anti-vapor lock capabilities. The gap 293 allows vapor, which would otherwise be stuck between the controlled freeze zone wall 46 and the overflow weir 215, to exit the space between the controlled freeze zone wall 46 and the overflow weir 215 and flow upwards toward the upper section 39 of the middle controlled freeze zone section 108. The gap 293 is wide enough to prevent solids from plugging the gap (e.g., greater than 0.5 cm). The gap 293 can also prevent solids from falling between the overflow weir 215 and the controlled freeze zone wall 46 to the lower section 106.

The underflow weir 216 may comprise a plurality of underflow weirs and/or the overflow weir 215 may comprise a plurality of overflow weirs 215. When the system comprises one or more underflow weirs 216 and/or one or more overflow weirs 215, the weirs may be positioned at any suitable place within the lower portion of the middle controlled freeze zone section 108. For example, one underflow weir 216 and one overflow weir 215 may be on a left side 46a of the controlled freeze zone wall 46 while a second underflow weir 216 and a second overflow weir 215 may be on a right side 46b of the controlled freeze zone wall 46.

In addition to the underflow weir 216 and overflow weir 215, and despite their potential limitations, the middle controlled freeze zone section 108 may comprise a liquid level indicator 212 (FIGS. 5-6). The liquid level indicator 212 may be constructed and arranged to detect the liquid level of the liquid 130. The liquid level indicator 212 may be any suitable liquid level indicator 212. For example, the liquid level indicator 212 may be at least one of differential pressure cells, guided wave radar sensors and a nucleonic mechanism. The nucleonic mechanism may comprise, for example, the radiation detector and radiation source disclosed in the application entitled "Method and Device for Separating a Feed Stream Using Radiation Detectors" (U.S. Ser. No. 61/912,964) by Jaime Valencia et al. and having the same priority date as this disclosure.

The middle controlled freeze zone section 108 may also comprise a spray assembly 129. The spray assembly 129 cools the vapor stream that rises from the lower section 40. The spray assembly 129 sprays liquid, which is cooler than the vapor stream, on the vapor stream to cool the vapor stream. The spray assembly 129 is within the upper section 39. The spray assembly 129 is not within the lower section 40. The spray assembly 129 is above the melt tray assembly 139. In other words, the melt tray assembly 139 is below the spray assembly 129.

The spray assembly 129 includes one or more spray nozzles 120 (FIGS. 1-4). Each spray nozzle 120 sprays liquid on the vapor stream. The spray assembly 129 may also include a spray pump 128 (FIGS. 1-4) that pumps the liquid. Instead of a spray pump 128, gravity may induce flow in the liquid.

The liquid sprayed by the spray assembly 129 contacts the vapor stream at a temperature and pressure at which solids form. The liquid may also contact the vapor stream at a composition at which solids form. Solids, containing mainly contaminants, form when the sprayed liquid contacts the vapor stream (FIG. 7). The solids fall toward the melt tray assembly 139.

The temperature in the middle controlled freeze zone section 108 cools down as the vapor stream travels from the bottom of the middle controlled freeze zone section 108 to the top of the middle controlled freeze zone section 108. The methane in the vapor stream rises from the middle controlled freeze zone section 108 to the upper section 110. Some contaminants may remain in the methane and also rise. The contaminants in the vapor stream tend to condense or solidify with the colder temperatures and fall to the bottom of the middle controlled freeze zone section 108.

The solids form the liquid and/or slurry mix when in the liquid 130. The liquid and/or slurry mix flows from the middle controlled freeze zone section 108 to the lower distillation section 106. The liquid and/or slurry mix flows from the bottom of the middle controlled freeze zone section 108 to the top of the lower section 106 via a line 22 (FIGS. 1-4). The line 22 may be an exterior line. The line 22 may extend from the distillation tower 104, 204. The line 22 may extend from the middle controlled freeze zone section 108. The line may extend to the lower section 106. The line 22 may extend from an outer surface of the distillation tower 104, 204.

The vapor stream that rises in the middle controlled freeze zone section 108 and does not form solids or otherwise fall to the bottom of the middle controlled freeze zone section 108, rises to the upper section 110. The upper section 110 operates at, at least one of a temperature, a pressure and a composition and contaminant concentration at which no solid forms. The upper section 110 is constructed and arranged to cool the vapor stream to separate the methane from the contaminants. Reflux in the upper section 110 cools the vapor stream. The reflux is introduced into the upper section 110 via line 18. Line 18 may extend to the upper section 110. Line 18 may extend from an outer surface of the distillation tower 104, 204.

After contacting the reflux in the upper section 110, the feed stream forms a vapor stream and a liquid stream. The vapor stream mainly comprises methane. The liquid stream comprises relatively more contaminants. The vapor stream rises in the upper section 110 and the liquid falls to a bottom of the upper section 110.

To facilitate separation of the methane from the contaminants when the stream contacts the reflux, the upper section 110 may include one or more mass transfer devices 176. Each mass transfer device 176 helps separate the methane from the contaminants. Each mass transfer device 176 may comprise any suitable separation device, such as a tray with perforations, or a section of random or structured packing to facilitate contact of the vapor and liquid phases.

After rising, the vapor stream may exit the distillation tower 104, 204 through line 14. The line 14 may emanate from an upper part of the upper section 110. The line 14 may extend from an outer surface of the upper section 110.

From line 14, the vapor stream may enter a condenser 122. The condenser 122 cools the vapor stream to form a cooled stream. The condenser 122 at least partially condenses the stream.

After exiting the condenser 122, the cooled stream may enter a separator 124. The separator 124 separates the vapor stream into liquid and vapor streams. The separator may be any suitable separator that can separate a stream into liquid and vapor streams, such as a reflux drum.

Once separated, the vapor stream may exit the separator 124 as sales product. The sales product may travel through line 16 for subsequent sale to a pipeline and/or condensation to be a liquefied natural gas.

Once separated, the liquid stream may return to the upper section 110 through line 18 as the reflux. The reflux may travel to the upper section 110 via any suitable mechanism, such as a reflux pump 150 (FIGS. 1 and 3) or gravity (FIGS. 2 and 4).

The liquid stream (i.e., freezing zone liquid stream) that falls to the bottom of the upper section 110 collects at the bottom of the upper section 110. The liquid may collect on tray 183 (FIGS. 1 and 3) or at the bottommost portion of the upper section 110 (FIGS. 2 and 4). The collected liquid may exit the distillation tower 104, 204 through line 20 (FIGS. 1 and 3) or outlet 260 (FIGS. 2 and 4). The line 20 may emanate from the upper section 110. The line 20 may emanate from a bottom end of the upper section 110. The line 20 may extend from an outer surface of the upper section 110.

The line 20 and/or outlet 260 connect to a line 41. The line 41 leads to the spray assembly 129 in the middle controlled freeze zone section 108. The line 41 emanates from the holding vessel 126. The line 41 may extend to an outer surface of the middle controlled freeze zone section 110.

The line 20 and/or outlet 260 may directly or indirectly (FIGS. 1-4) connect to the line 41. When the line 20 and/or outlet 260 directly connect to the line 41, the liquid spray may be pumped to the spray nozzle(s) 120 via any suitable mechanism, such as the spray pump 128 or gravity. When the line 20 and/or outlet 260 indirectly connect to the line 41, the lines 20, 41 and/or outlet 260 and line 41 may directly connect to a holding vessel 126 (FIGS. 1 and 3). The holding vessel 126 may house at least some of the liquid spray before it is sprayed by the nozzle(s). The liquid spray may be pumped from the holding vessel 126 to the spray nozzle(s) 120 via any suitable mechanism, such as the spray pump 128 (FIGS. 1-4) or gravity. The holding vessel 126 may be needed when there is not a sufficient amount of liquid stream at the bottom of the upper section 110 to feed the spray nozzles 120.

It is important to note that the steps depicted in FIG. 7 provided for illustrative purposes only and a particular step may not be required to perform the inventive methodology. The claims, and only the claims, define the inventive system and methodology.

Disclosed aspects may be used in hydrocarbon management activities. As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. The term "hydrocarbon management" is also used for the injection or storage of hydrocarbons or $CO_2$, for example the sequestration of $CO_2$, such as reservoir evaluation, development planning, and reservoir management. The disclosed methodologies and techniques may be used to produce hydrocarbons in a feed stream extracted from, for example, a subsurface region. The feed stream extracted may be processed in the distillation tower 104, 204 and separated into methane and contaminants. The separated methane exits the middle controlled freeze zone section 108 or the upper section 110 of the distillation tower. Some or all of the methane that exits is produced as produced hydrocarbons, 307 (FIG. 7). Hydrocarbon extraction may be conducted to remove the feed stream from, for example, the subsurface region, which may be accomplished by drilling a well using oil well drilling equipment. The equipment and techniques used to drill a well and/or extract the hydrocarbons are well known by those skilled in the relevant art. Other hydrocarbon extraction activities and, more generally, other hydrocarbon management activities, may be performed according to known principles.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described and considered to be within the scope of the disclosure.

It should be understood that numerous changes, modifications, and alternatives to the preceding disclosure can be made without departing from the scope of the disclosure. The preceding description, therefore, is not meant to limit the scope of the disclosure. Rather, the scope of the disclosure is to be determined only by the appended claims and their equivalents. It is also contemplated that structures and features in the present examples can be altered, rearranged, substituted, deleted, duplicated, combined, or added to each other.

The articles "the", "a" and "an" are not necessarily limited to mean only one, but rather are inclusive and open ended so as to include, optionally, multiple such elements.

What is claimed is:

1. A method of maintaining a liquid level in a distillation tower, the method comprising:
    forming a freezing zone vapor stream from a feed stream in a stripper section of a distillation tower at a temperature and pressure at which no solid forms in the stripper section;
    forming a solid in a controlled freeze zone section of the distillation tower from the feed stream;
    preventing accumulation of solid in the controlled freeze zone section by at least providing:
        a melt tray assembly in the controlled freeze zone section that includes a liquid, melt tray, and bubble cap;
        an underflow weir in the controlled freeze zone section that alters a flow of the liquid in the melt tray assembly;
        an overflow weir in the controlled freeze zone section that works with the underflow weir to alter the flow of the liquid in the melt tray assembly and is adjacent to the underflow weir;
        a covering element in the controlled freeze zone section that is connected to and extends from the underflow weir, over the overflow weir, and towards the controlled freeze zone wall;
    maintaining a predetermined liquid level of liquid in a melt tray assembly of the controlled freeze zone section by:
        altering a flow of the liquid in the melt tray assembly such that the liquid flows from a bottom melt tray assembly portion of the melt tray assembly to a top melt tray assembly portion of the melt tray assembly; and
        altering the flow of the liquid in the melt tray assembly such that the liquid flows from the top melt tray assembly portion toward the stripper section; and
    closing a flow control device that connects the stripper section and the controlled freeze zone section such that the level of the liquid in the melt tray assembly rises and is greater than the predetermined liquid level and such that the liquid acts to melt solids that have accumulated in the controlled freeze zone above the predetermined liquid level.

2. The method of claim 1, further comprising directing vapor that accumulated while altering the flow of the liquid, upwards toward a top section of the controlled freeze zone section.

3. The method of claim 1, further comprising producing hydrocarbons from the feed stream.

4. The method of claim 1, wherein the covering element is at an angle of from 1 to 45 degrees relative to the controlled freeze zone wall.

5. The method of claim 1, further comprising preventing an accumulation of vapor in the controlled freeze zone section by at least providing an anti-vapor lock that is connected to and extends from the controlled freeze zone wall toward the covering element, where there is a gap between the end of the anti-vapor lock that is closest to the covering element and the covering element.

6. The method of claim 5, wherein the anti-vapor lock extends from the controlled freeze zone wall at an angle of from 1 to 45 degrees relative to the controlled freeze zone wall.

7. A method for modifying a liquid level in a distillation tower, the method comprising:
   providing a distillation tower, wherein the distillation tower comprises:
     a stripper section constructed and arranged to separate a feed stream at a temperature and pressure at which the feed stream forms no solid;
     a controlled freeze zone section constructed and arranged to separate the feed stream at a temperature and pressure at which the feed stream forms a solid, wherein the controlled freeze zone section includes a controlled freeze zone wall;
     a melt tray assembly in the controlled freeze zone section that includes a liquid, melt tray, and bubble cap;
     an underflow weir in the controlled freeze zone section that alters a flow of the liquid in the melt tray assembly;
     an overflow weir in the controlled freeze zone section that works with the underflow weir to alter the flow of the liquid in the melt tray assembly and is adjacent to the underflow weir;
     a covering element in the controlled freeze zone section that is connected to and extends from the underflow weir, over the overflow weir, and towards the controlled freeze zone wall;
     an anti-vapor lock that is connected to and extends from the controlled freeze zone wall toward the covering element, where there is a gap between the end of the anti-vapor lock that is closest to the covering element and the covering element;
     a channel connecting the stripper section to the controlled freeze zone section; and
     a flow control device to control the flow of liquid from the controlled freeze zone section to the stripper section;
   forming a freezing zone vapor stream from the feed stream in the stripper section;
   forming a solid in the controlled freeze zone section from the feed stream;
   modifying the liquid level in the melt tray assembly by opening or closing the flow control device, wherein when the flow control device is open the maximum level of liquid in the melt tray assembly is at a predetermined height that is determined by the height of the overflow weir, and wherein when the flow control device is closed the maximum level of liquid in the melt tray assembly is greater than the predetermined height and is greater than the height of the bubble cap; and
   closing the flow control device for a period of time that is sufficient to melt solids that have accumulated in the controlled freeze zone above the predetermined height.

8. The method of claim 7, wherein the period of time is from five minutes to thirty minutes.

9. The method of claim 7, wherein the channel comprises at least one of an internal channel and an external channel.

10. The method of claim 9, wherein the internal channel is inside of the controlled freeze zone section and the stripper section and wherein the internal channel includes the overflow weir.

* * * * *